(12) United States Patent
McLoughlin et al.

(10) Patent No.: US 11,497,685 B2
(45) Date of Patent: Nov. 15, 2022

(54) COMBINATORIAL DRUG DELIVERY DEVICE

(71) Applicant: Bristol-Myers Squibb Company, Princeton, NJ (US)

(72) Inventors: Martin John McLoughlin, Hillsborough, NJ (US); Chester Larrow, Baltimore, MD (US); Mariano Mumpower, Baltimore, MD (US)

(73) Assignee: Bristol-Myers Squibb Company, Princeton, NJ (US)

( * ) Notice: Subject to any disclaimer, the term of this patent is extended or adjusted under 35 U.S.C. 154(b) by 89 days.

(21) Appl. No.: 17/047,449

(22) PCT Filed: May 10, 2019

(86) PCT No.: PCT/US2019/031791
§ 371 (c)(1),
(2) Date: Oct. 14, 2020

(87) PCT Pub. No.: WO2019/217864
PCT Pub. Date: Nov. 14, 2019

(65) Prior Publication Data
US 2021/0145696 A1 May 20, 2021

Related U.S. Application Data

(60) Provisional application No. 62/670,266, filed on May 11, 2018.

(51) Int. Cl.
*A61J 1/20* (2006.01)
*A61M 5/14* (2006.01)
*A61M 5/142* (2006.01)

(52) U.S. Cl.
CPC ............ *A61J 1/2089* (2013.01); *A61J 1/201* (2015.05); *A61J 1/2058* (2015.05); *A61J 1/2075* (2015.05);

(Continued)

(58) Field of Classification Search
CPC ........ A61J 1/2089; A61J 1/201; A61J 1/2058; A61M 5/1407
See application file for complete search history.

(56) References Cited

U.S. PATENT DOCUMENTS

| | | | | |
|---|---|---|---|---|
| 4,085,782 A | * | 4/1978 | Carlson | B65B 3/003 222/400.7 |
| 5,037,390 A | * | 8/1991 | Raines | A61J 3/002 211/74 |

(Continued)

FOREIGN PATENT DOCUMENTS

| | | |
|---|---|---|
| EP | 2236199 A2 | 10/2010 |
| WO | 2007107406 A2 | 9/2007 |
| WO | 2012092564 A2 | 7/2012 |

OTHER PUBLICATIONS

International Search Report and Written Opinion of the International Searching Authority from PCT International Application No. PCT/US2019/031791, dated Oct. 10, 2019.

*Primary Examiner* — Catharine L Anderson
*Assistant Examiner* — Arjuna P Chatrathi
(74) *Attorney, Agent, or Firm* — Budzyn IP Law, LLC

(57) ABSTRACT

In one aspect, a combinatorial drug delivery device is provided for delivering a predetermined selection of drug components. The device includes a plurality of modules, each including: a body having an interior volume; a spike plate movably disposed in the interior volume, the spike plate having a protruding cannula and first and second ports. The device also includes a base tray which includes: a framework defining a plurality of wells, each of the wells formed to insertingly receive one of the modules; for each of the wells, first and second inlet ports formed to interface with the first and second ports of the module being received in the respective well; passageways to connect certain wells with adjacent wells to permit fluid flow therebetween. For (Continued)

each of the wells, the spike plate of the respective module being maintained in a stationary position with the module being inserted into the well.

10 Claims, 15 Drawing Sheets

(52) U.S. Cl.
CPC ........ *A61M 5/1407* (2013.01); *A61M 5/1408* (2013.01); *A61M 5/1409* (2013.01); *A61M 5/1413* (2013.01); *A61M 5/14248* (2013.01); *A61J 1/2068* (2015.05)

(56) References Cited

U.S. PATENT DOCUMENTS

| | | | | |
|---|---|---|---|---|
| 5,122,116 | A * | 6/1992 | Kriesel | A61M 5/1409 604/416 |
| 5,329,976 | A * | 7/1994 | Haber | A61J 1/2096 604/407 |
| 7,442,181 | B2 * | 10/2008 | Schubert | A61M 5/1413 604/65 |
| 7,963,945 | B2 * | 6/2011 | Miller | A61M 5/16827 604/131 |
| 9,132,228 | B2 * | 9/2015 | Yan | B05B 1/14 |
| 2002/0004643 | A1 | 1/2002 | Carmel et al. | |
| 2008/0164273 | A1 * | 7/2008 | Dallman | A61J 7/0069 221/2 |
| 2009/0062732 | A1 * | 3/2009 | Radmer | A61M 5/1409 604/84 |
| 2012/0089088 | A1 * | 4/2012 | Foshee | A61J 1/2089 53/425 |
| 2012/0184938 | A1 * | 7/2012 | Lev | B65D 51/002 604/414 |
| 2012/0184939 | A1 * | 7/2012 | Reiter | A61M 5/1409 604/151 |
| 2013/0253430 | A1 | 9/2013 | Kouyoumjian et al. | |
| 2013/0255834 | A1 * | 10/2013 | Fini | B65B 3/003 604/411 |
| 2014/0261727 | A1 * | 9/2014 | Mansour | A61J 1/20 137/15.01 |
| 2015/0257974 | A1 | 9/2015 | Demers et al. | |
| 2015/0258275 | A1 * | 9/2015 | Kotzur | A61M 5/16813 604/246 |
| 2017/0007501 | A1 * | 1/2017 | Schuldt-Lieb | A61J 1/2089 |
| 2017/0020784 | A1 * | 1/2017 | Schweiss | A61J 1/2089 |

* cited by examiner

COMBINATORIAL DRUG DELIVERY DEVICE

FIELD OF THE INVENTION

The field of the present invention is the compounding and preparation of liquid drugs, especially for intra-venous infusion and direct patient administration. More particularly the invention relates to devices for the preparation and compounding of combinations of two or more drugs.

BACKGROUND OF THE INVENTION

It is common practice in the administration of drugs by intravenous infusion for the drugs to be compounded within a pharmacy environment. Such drugs are typically supplied sterile in glass vials and may be supplied in solid or aqueous solution form. When supplied in solid form the drugs must be reconstituted with a sterile aqueous diluent prior to transfer to the infusion bag. The person skilled in the art will appreciate that such drug formulations will typically include several excipients for example buffers, pH modifiers, tonicity modifiers, stabilizers and so on. Typically liquid drugs for intra-venous infusion are compounded in an infusion bag in a pharmacy environment prior to transfer to the patient for infusion. Because of the need to maintain sterility of the drugs while compounding the compounding procedure is typically performed in an aseptic pharmacy hood. Typically the pharmacist or pharmacy technician (practitioner) will prepare the drugs in accordance with an individual patient prescription.

After ensuring the hood is clear of all materials the practitioner will retrieve vials of the drugs required per the prescription from the pharmacy stocks and will verify their identity and strength. The verification process may be assisted by use of a bar code scanner or other identification technology. The practitioner will also pick from stock all of the other necessary equipment required to safely prepare the drugs for infusion including the infusion bag itself, syringes, needles, transfer sets, gloves, sharps disposal containers and so on. Once all of the necessary equipment has been assembled the practitioner will follow a protocol for the preparation of the drugs which may include the reconstitution of solid drugs by addition of diluents, the ordered withdrawal of liquid drugs from their individual vials into the IV bag via the transfer port. Typically this procedure is performed manually and involves the use of multiple needles. The risk of needle-stick injuries to the practitioner is increased by each needle required to effect the compounding of the drugs. With high potency or toxicity drugs, e.g. cytotoxic agents for chemotherapy, this presents a considerable exposure risk for the practitioner.

To eliminate some of the risks associated with manual preparation including exposure to dangerous drugs and the risk of medication errors, pharmacy compounding machines are known to the person skilled in the art which automate many of the steps involved in the preparation and compounding of drugs. Typically such machines are complex electromechanical systems which implement sophisticated precision dispensing mechanisms for the accurate reconstitution of liquid drugs. Aside from their cost, size and complexity, many of the designs for such machines described in the art draw liquid drugs from a stock reservoir and so only use a fraction of the drug in the container. Because of the need to maintain sterility, unused drug solutions must typically be discarded and so are wasted. With the very high cost of some drugs, especially biologic drugs, this waste is a significant undesirable cost. When the wasted drugs are cytotoxic agents, their disposal creates a significant environmental and safety hazard.

Recent advances in medicine, particularly in the treatment of cancer, have demonstrated that therapeutically beneficial effects can be achieved by the synergistic combination of two or more drugs. For example, recent clinical research has demonstrated that the combination of an anti-PD-1 checkpoint inhibitor drug with a CTLA-4 checkpoint inhibitor can have beneficial synergistic effects in some tumor types which can lead to better clinical outcomes than could be achieved by the individual administration of either drug alone. Typically such checkpoint inhibitor drugs are biotechnology derived monoclonal antibodies or fragments thereof of the immunoglobulin type. In some situations it may be beneficial to combine such biologic drugs with conventional chemotherapy agents such as cytotoxic drugs.

Applicant has now realized that the combinatorial principles described in U.S. Provisional Patent Application No. 62/670,266, filed on May 11, 2018, to the same assignee as herein, and which is incorporated herein by reference in its entirety, can address several of the challenges encountered in the preparation and compounding of drugs for intra-venous infusion and can provide several advantages including but not limited to simplification of pharmacy procedures, reduction in the risk of medication errors, containment and protection for the practitioner from highly potent or highly toxic agents, reduction in the risk of needle-stick injuries, reduction or elimination of drug waste, avoidance of the need for complex and expensive pharmacy compounding machines. As a consequence of these advantages in embodiments the present invention may further enable the preparation and compounding of drugs for IV infusion and direct administration to a patient at locations remote from the pharmacy, and by a non-specialist practitioner, for example by a suitably trained technician or nurse at the patient's home. This possibility is enhanced by the intrinsic portability of the system described herein.

SUMMARY OF THE INVENTION

According to the present invention, there are provided drug modules, which are inserted and mechanically locked into a provided common base tray, which fluidically connects all inserted modules and delivers all modules' contents.

Each module defines a chamber for the receipt of a drug-filled vial and in embodiments, spacing adapters may be provided to enable the receipt of different sized vials. The modules further comprise a hinged cap to allow access to the vial septum for disinfection. Within the hinged cap, a floating vial spike plate with protruding spike having inlet and outlet ports is captured allowing for only axial travel, permitting the spike to breach the vial septum upon insertion of the module into the base tray.

The base tray consists of several prearranged wells designed to accept the hinged cap geometry of the modules. Within each well are two check valve styled fluidic connection ports that interface with the input and output ports of the module vial spike plate. By sufficiently pressing the vial spike plate into the base tray's valves, a fluidic connection is made between the base tray valves through the vial spike plate. Internally, sterile tubing is used to fluidically connect a single check valve in adjacent wells to create a fluidic circuit, which is only completed once all the wells of the base tray have been filled with the specified modules. The base tray will contain an air filter and/or vent which will terminate one end of the internal fluidic circuit. The fluidic circuit of the base tray will flow the drug product from the modules out a sterilized main output line from the base tray. A one-way valve in the main output line will prevent drug product from back flushing into the base tray.

Cooperating mechanical keying features present on both the internal walls of the base tray wells and the outer surface of the module's hinged cap create a poka yoke mechanism that will ensure that modules may only be inserted into prescribed wells of the base tray. In embodiments, module placement within the base tray may be controlled and monitored by electronic means.

The main output line from the base tray may be terminated by a sterile hollow needle which may be used to breach the sterile port on an infusion bag or other container for the pumped transfer of liquid drugs into the container or may be used for drug administration directly into a patient. Further, a pump may be provided so that, when fully connected, the liquid drugs in the vials may be pumped as one collective output from their respective vials into the bag, container, or patient.

The pump may be integral to the base tray or may be external to the base tray. The pump may be sterile and form a component of the fluid path or may be of the non-contacting variety such as peristaltic pumps. The person skilled in the art will be familiar with several pumping technologies suitable for use in the pumped transfer of liquid drugs in the manner described.

DETAILED DESCRIPTION

With reference to the Figures, modules 12 and base tray 14 formed in accordance with the subject invention are shown, modules 12 are serially connected once installed into the base tray 14 to form a combinatorial drug delivery device 10. To minimize the number of components needed in inventory, it is preferred that the modules 12 be similarly formed. The modules 12 may be formed with adjustable features to correspond to any contained drugs to allow for verification of accuracy in use.

Figure 28A:
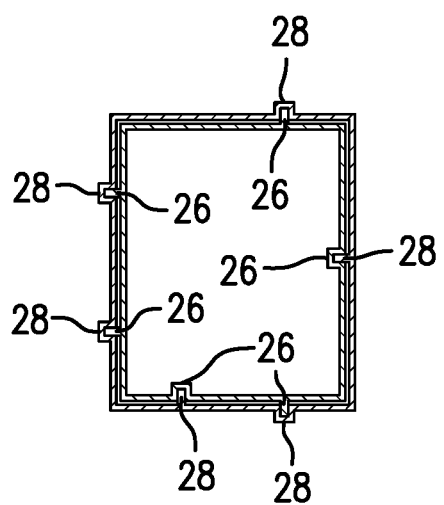
FIGS. 28A and 28B show schematically matching and non-matching keying features.
Figure 28B:
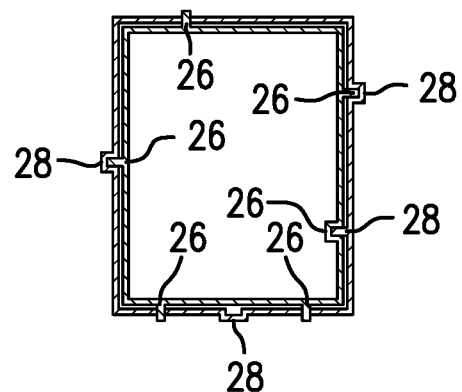

As shown in FIGS. 1-5, each of the modules 12 is generally box shaped with a body 16 and a lid 18 collectively enclosing an interior volume 20. The lid 18 may be hingedly attached to the body 16 so as to be selectively opened to access the interior volume 20. The interior volume 20 is shaped and dimensioned to accommodate a drug vial or container 22. To accommodate drug vials 22 of various sizes, adapter(s) or spacer(s) may be provided for placement into the interior volume 20 to accommodate various sized drug vials. The interior volume 20 may be configured to accommodate a largest drug vial size without any adapters or spacers. Outer surface 24 of the lid 18 may have protruding keying features 26, formed to interface with corresponding tray keying features 28 formed on an inner surface 30 of any well 32 of the base tray 14 in order to control the placement of specific modules within the fluidic serial connection of the base tray 14. The keying features 26 may be ridges and/or channels with the tray keying features 28 being ridges and/or channels patterned (sized and arranged) to only allow insertion therein of a module 12 having the keying features 26 in the same pattern. As shown schematically in FIGS. 28A and 28B, possible arrangements of the keying features 26, 28 are shown. As will be recognized by those skilled in the art, non-matching keying features 26, 28, such as shown in FIG. 28B, prevent insertion of a module 12 into a well 32. In contrast, matching keying features 26, 28, such as shown in FIG. 28A, allow for insertion of a module 12 into a well 32.

Figure 1:
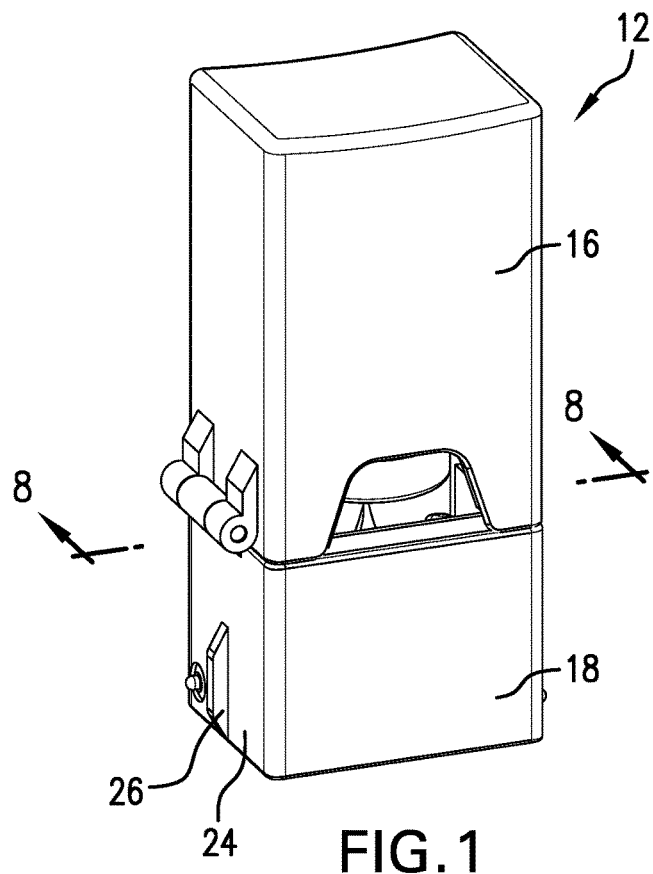
FIGS. 1-5 show a module formed in accordance with the subject invention.
Figure 2:
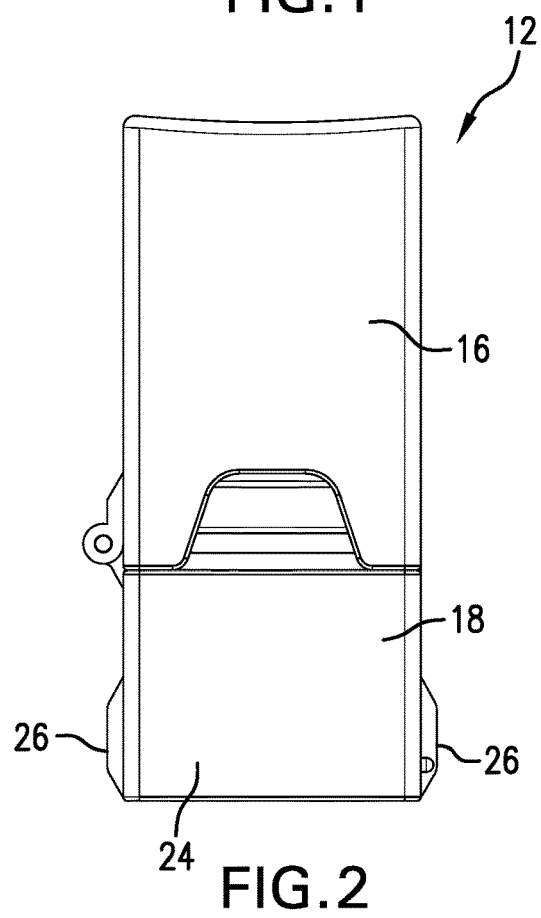
Figure 3:
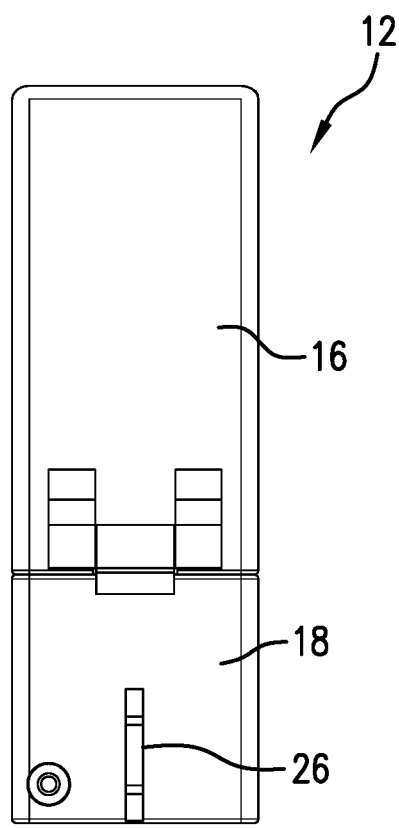
Figure 4:
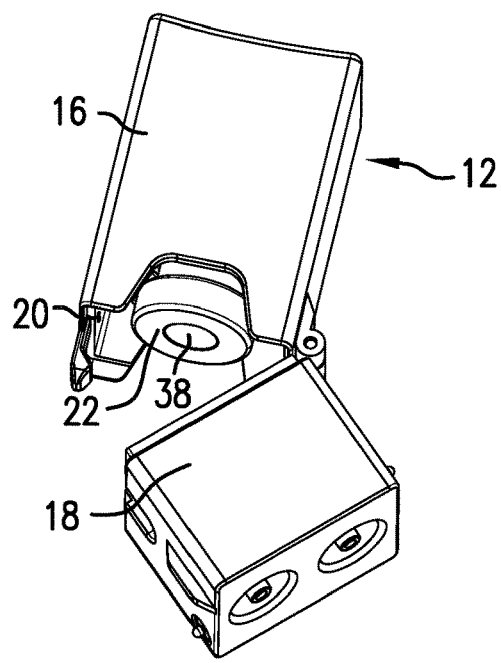
Figure 5:
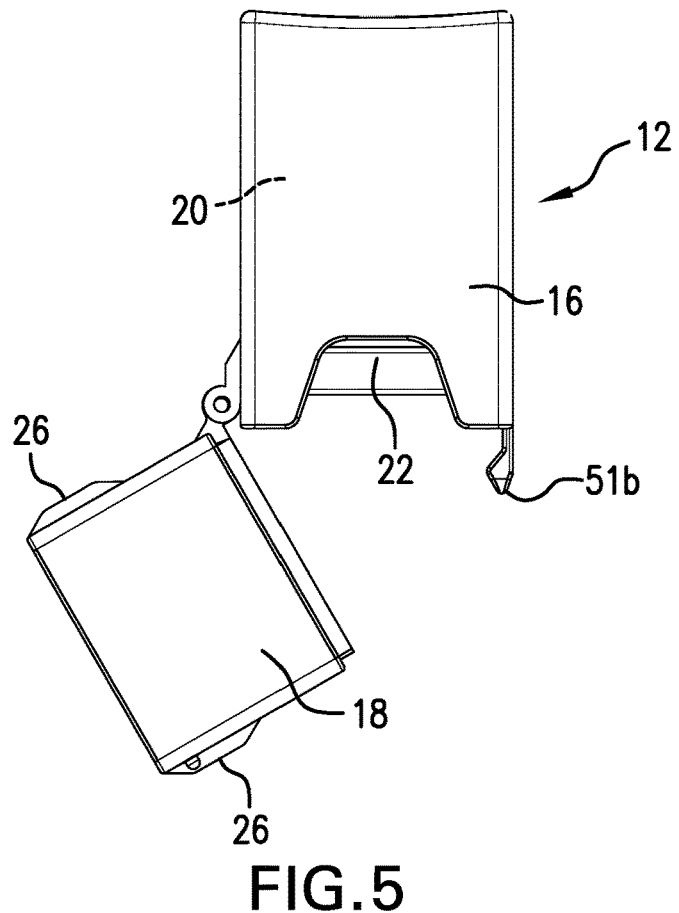
Figure 6:
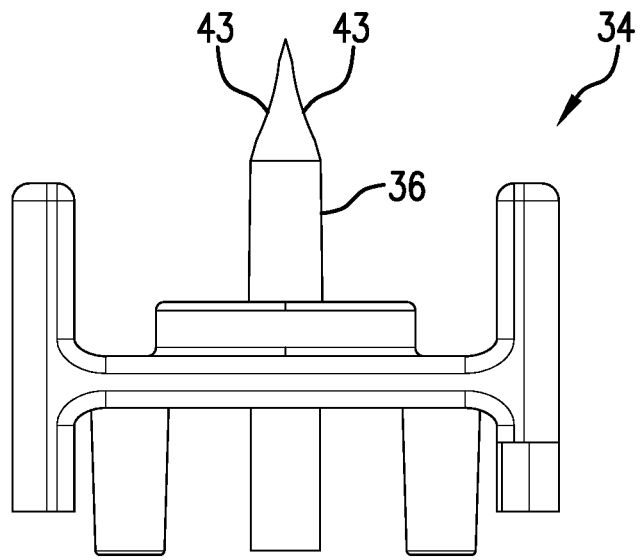
FIGS. 6-7 show a spike plate useable with the subject invention.
Figure 7:
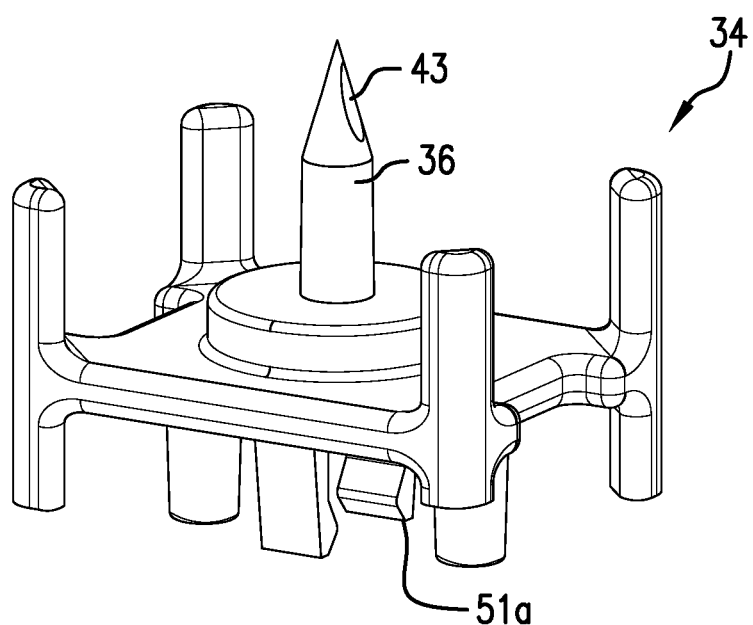
Figure 8:
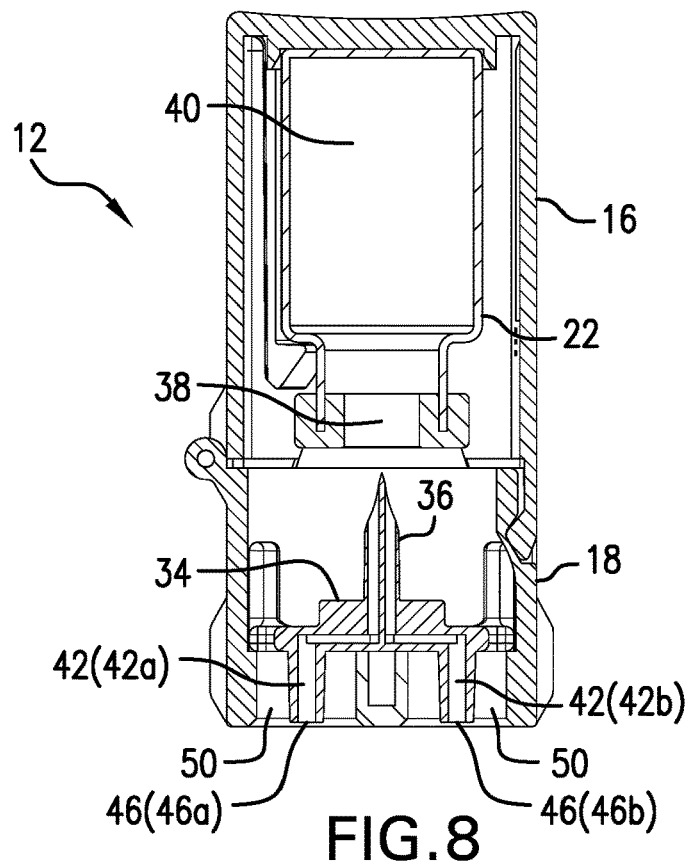
FIG. 8 is a cross-sectional view taken along line 8-8 of FIG. 1.
Figure 9:
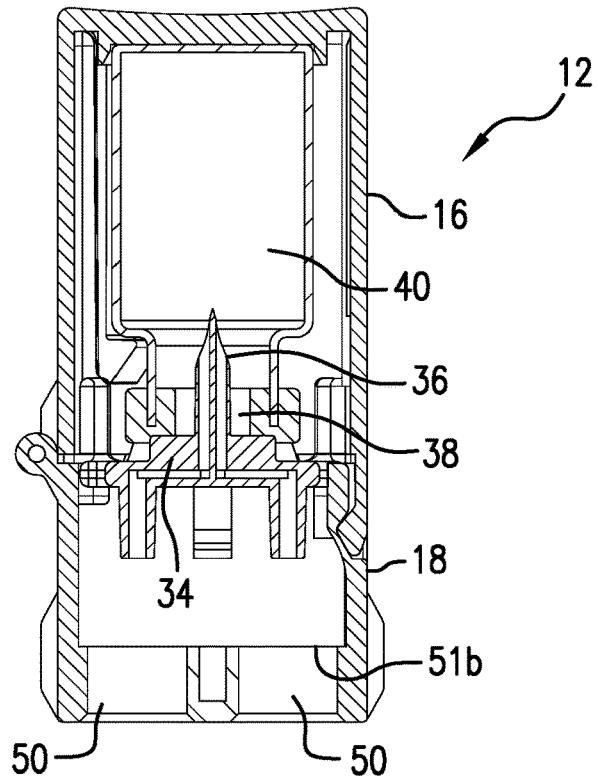
FIG. 9 is a similar view to FIG. 8 showing the spike piercing the septum of the drug vial.

As shown in FIGS. 8-9, each of the modules 12 includes a vial spike plate 34 captured within the hinged lid 18. When the lid 18 is closed the vial spike plate 34 has the ability to slide vertically within the module 12 extending spike 36 into the interior volume 20 positioned to pierce a septum 38 of an accommodated drug vial 22 in accessing inner volume 40 of the drug vial 22 (FIG. 9). The vial spike 36 may be sharpened to facilitate piercing of the septum 38. The spike 36 must be provided with sufficient length to fully pierce the septum 38 in accessing the inner volume 40 of the drug vial 22. The spike 36 preferably includes multiple inner lumens 42, such as primary inner lumen 42a and secondary inner lumen 42b, extending from distal openings 43. With this arrangement, with the spike 36 piercing the septum 38, all of the inner lumens 42, via the distal openings 43, are in communication with the inner volume 40 of the drug vial 22. The inner lumens 42 extend through the spike 36 away from distal end 44 and into the spike plate 34 ending at two fluid ports 46 (46a, 46b) proximal to the spike 36. The fluid ports 46 are formed to interface with inlet ports 48 (48a, 48b) of the base tray 14 through openings 50 in the lid 18. With this arrangement, liquid may flow in and out of the inner volume 40, e.g., with one-way flow travelling from one inlet port 48a, through the primary inner lumen 42a, into the inner volume 40, through the secondary inner lumen 42b, and into second inlet port 48b. This allows for both introduction of liquid into the drug vial 22 and removal of liquid therefrom. Seals may be provided to seal the interfaces between the ports 46 and the inlet ports 48.

To limit ingress of contaminants through the inlet ports 48, check valving 52, preferably one-way check valving, may be provided to normally seal closed the inlet ports 48. The ports 46 may be formed to be inserted into the inlet ports 48 thereby pushing open the check valves 52 to allow for open communication between the ports 46 and the inlet ports 48. As appreciated by those skilled in the art, any form of one-way check valve may be utilized, including, but not limited to, a spring-based check valve ball configured to seat in a normally-closed state. Passageways 54, which may be in the form of tubing, are in communication with each of the inlet ports 48 to deliver and receive liquid flow to and from the ports 48.

As shown in FIGS. 13-16, the base tray 14 consists of a framework of wells 32, each formed to accommodate one of the modules 12. It is preferred that a plurality of the wells 32 be provided to allow for a plurality of drug vials 32 to be utilized in having contents thereof mixed in a combined dosing. A pair of the inlet ports 48 is located in each of the wells 48, particularly protruding upwardly from a base 53. An upstanding wall 56 bounds each of the bases 53 in partially enclosing the wells 32. The inner surface 30, including the tray keying features 28, may be defined on interior portions of the walls 56. The walls 56 need to define a footprint which allows insertion of the modules 12 into the wells 32 with the keying features 26, 28 limiting access to particular sites if utilized. In this manner, specific arrangements of the modules 12, including the corresponding drug vials 22, may be ordered. This allows for combinatorial drug preparation by dictating which drug components (i.e., drug vials) are to be utilized, with also the higher level of arranging the components in a particular order. This provides an end user with a fail-safe check against improper inclusion of components and/or improper ordering.

Figure 12:
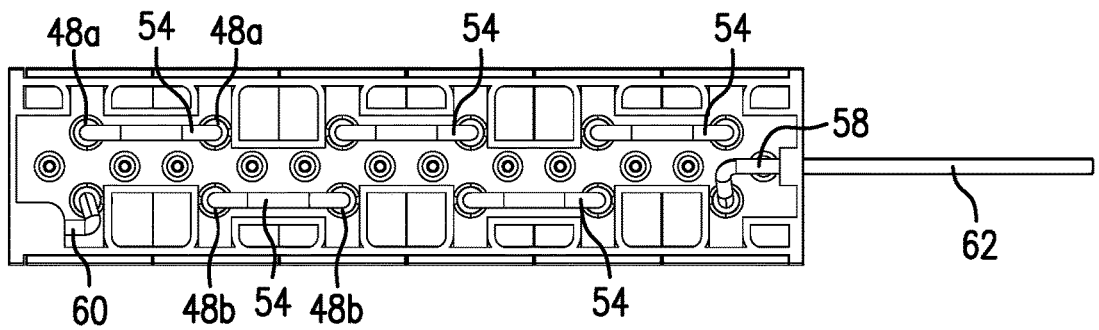
Figure 13:
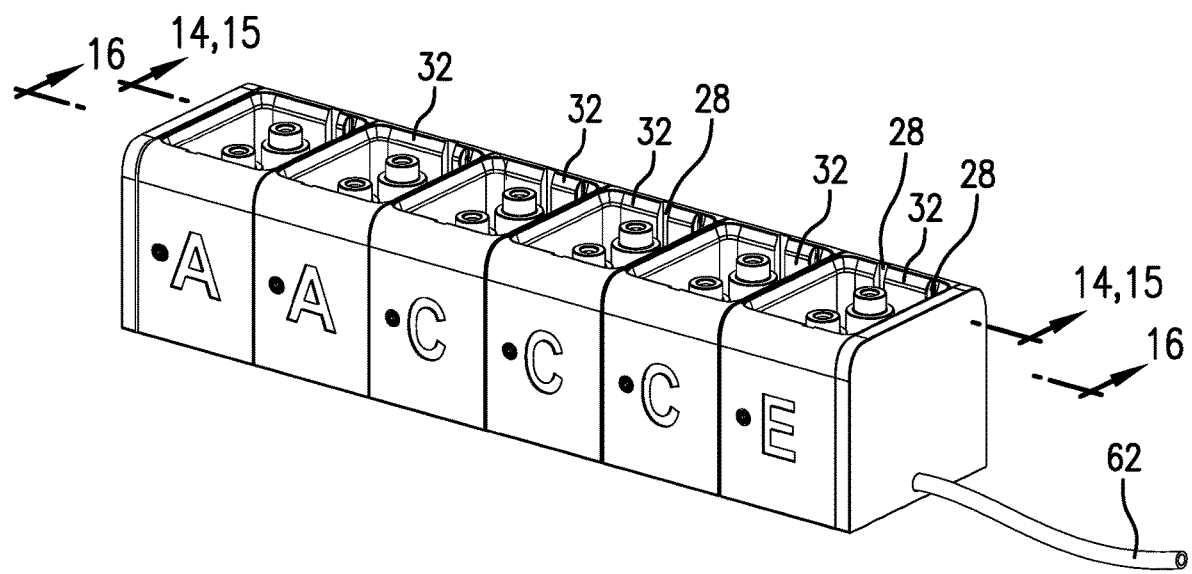
Figure 14:
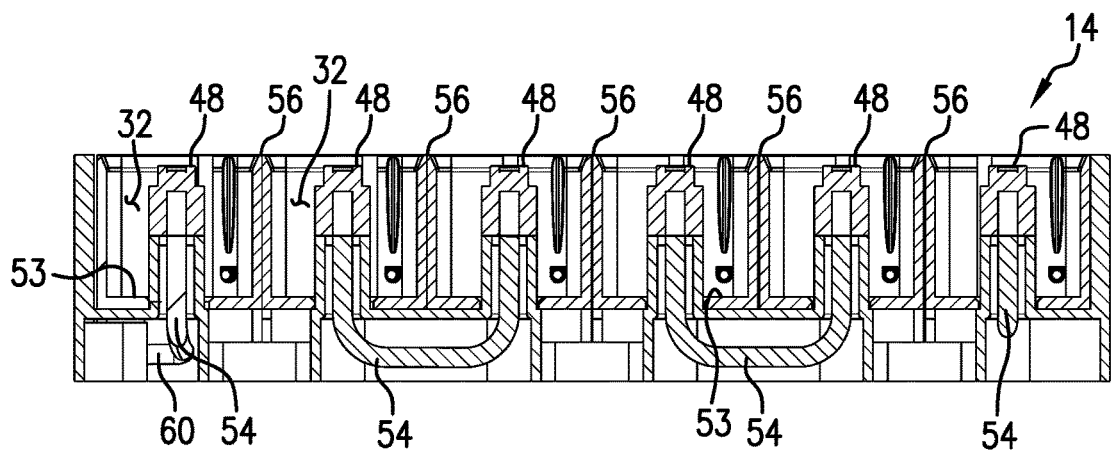
FIGS. 14, 15 and 16 are cross-sectional views taken along lines 14-14, 15-15, and 16-16, respectively, of FIG. 13.
Figure 15:
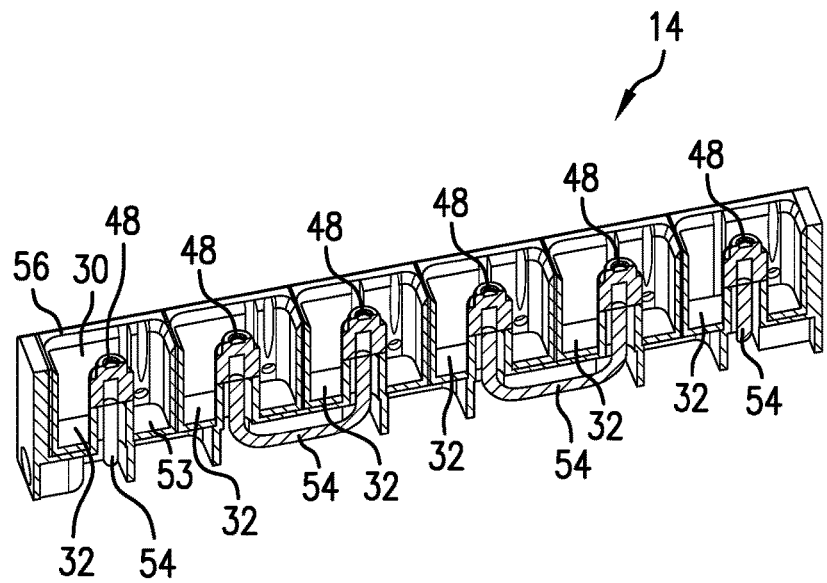
Figure 16:
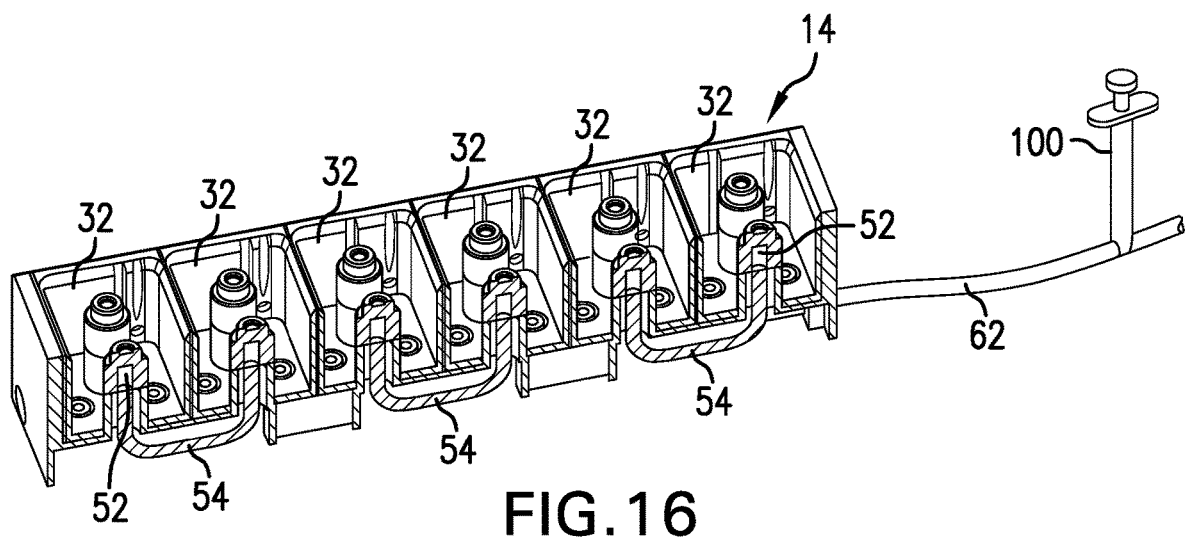

To allow for liquid flow between the wells 32, the passageways 54 are arranged in series between the inlet ports 48 to define a continuous fluid pathway through the base tray 14, with modules 12 being engaged in the wells 32. In particular, with reference to FIG. 12, the passageways 54 are connected to one inlet port 48b of one well 32 and extended to one inlet port 48a of an adjacent well 32, thus acting as an outlet for the first-mentioned well 32 and as an inlet for the second-mentioned well 32. The wells 32 at the end of the base tray 14 may include a common outlet 58, and a vent 60, if necessary.

The vent 60 may be terminated by an aseptic particulate filter embedded within the base tray 14. The filter may be configured to allow atmospheric air into the base tray fluidic path, while restricting ingress of microbes and other contaminants, in order to displace the fluid volume lost during evacuation of drug product from the modules 12 out of the sterilized main output line from the base tray 14. The vent 60 may be located at the end away from the common outlet 58 to provide venting for the full length of the fluid pathway. A one-way valve may be provided with the common outlet 58 to prevent drug product from back flushing into the base tray 14. The vent 60 may be necessary where the drug vials 22 are of rigid construction (e.g., polymeric or glass construction). With the drug vials 22 being collapsible (such as flexible bag construction), venting may not be necessary.

Figure 17:
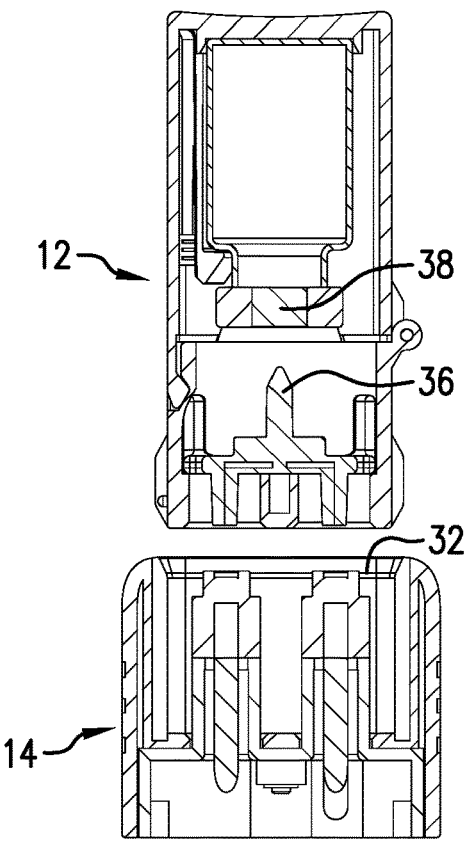
FIGS. 17-19 show insertion of a module into a well of the base tray.
Figure 18:
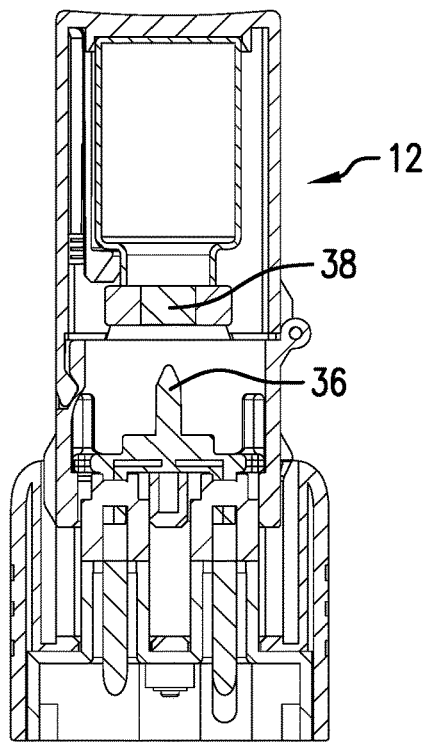
Figure 19:
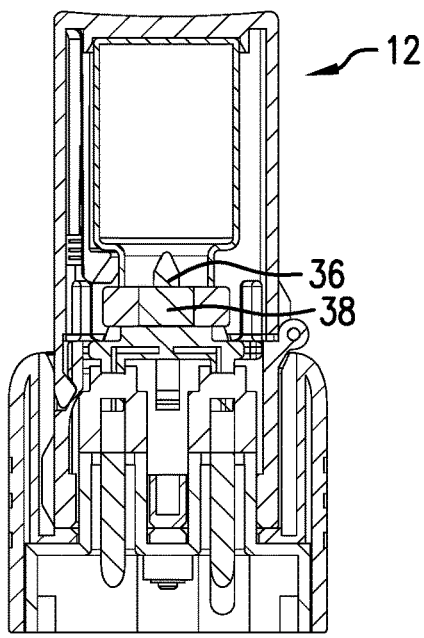
Figure 20:
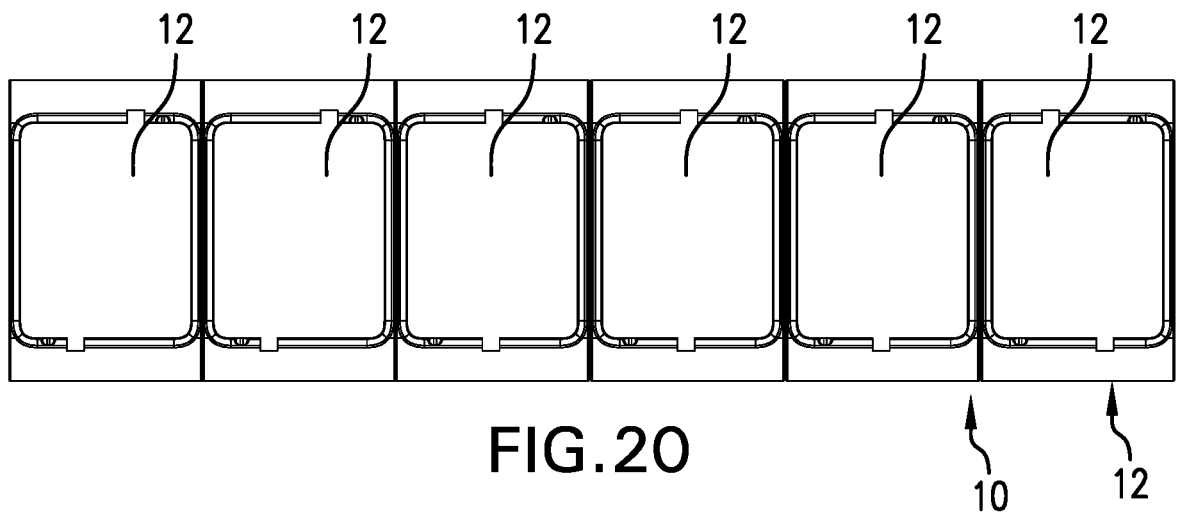
FIGS. 20-27 show different assemblies of modules and the base tray.
Figure 21:
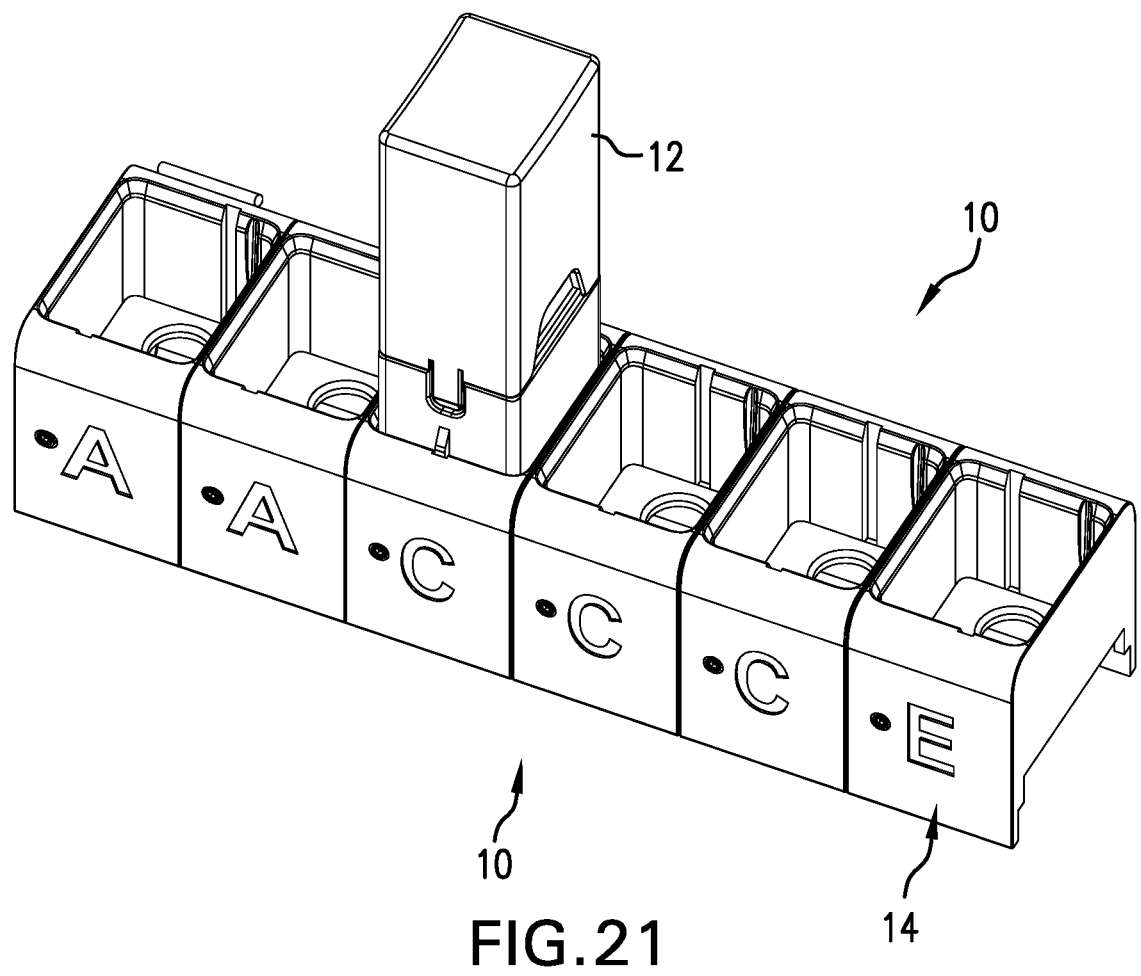
Figure 22:
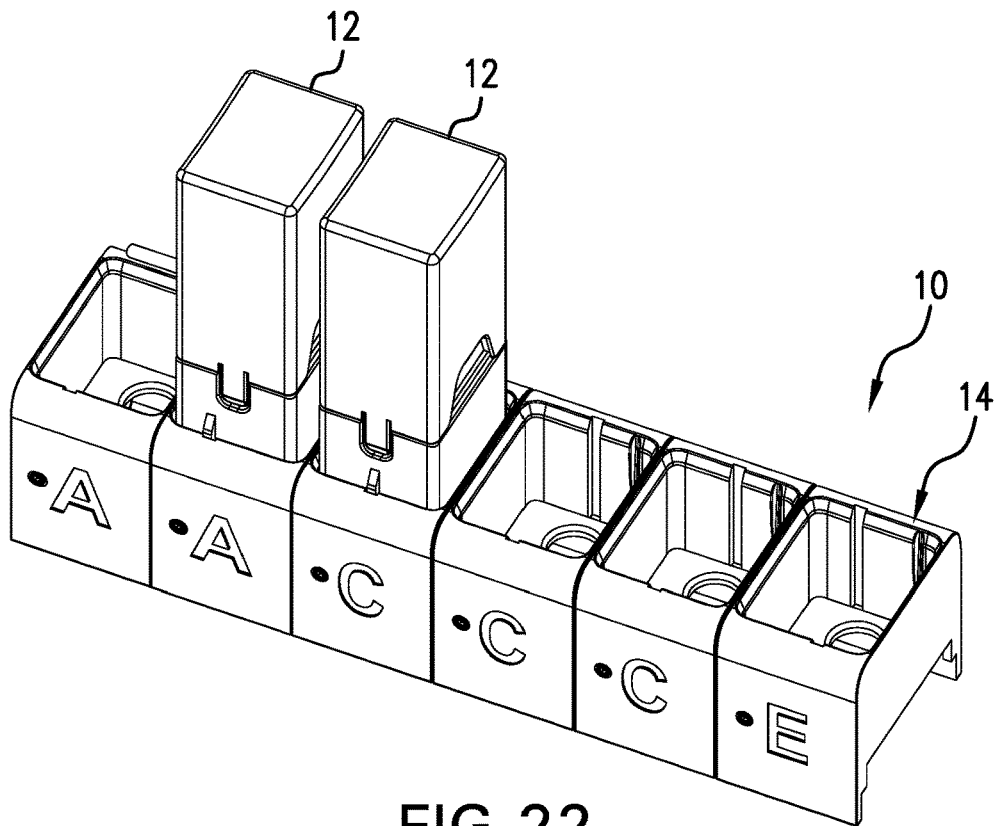
Figure 23:
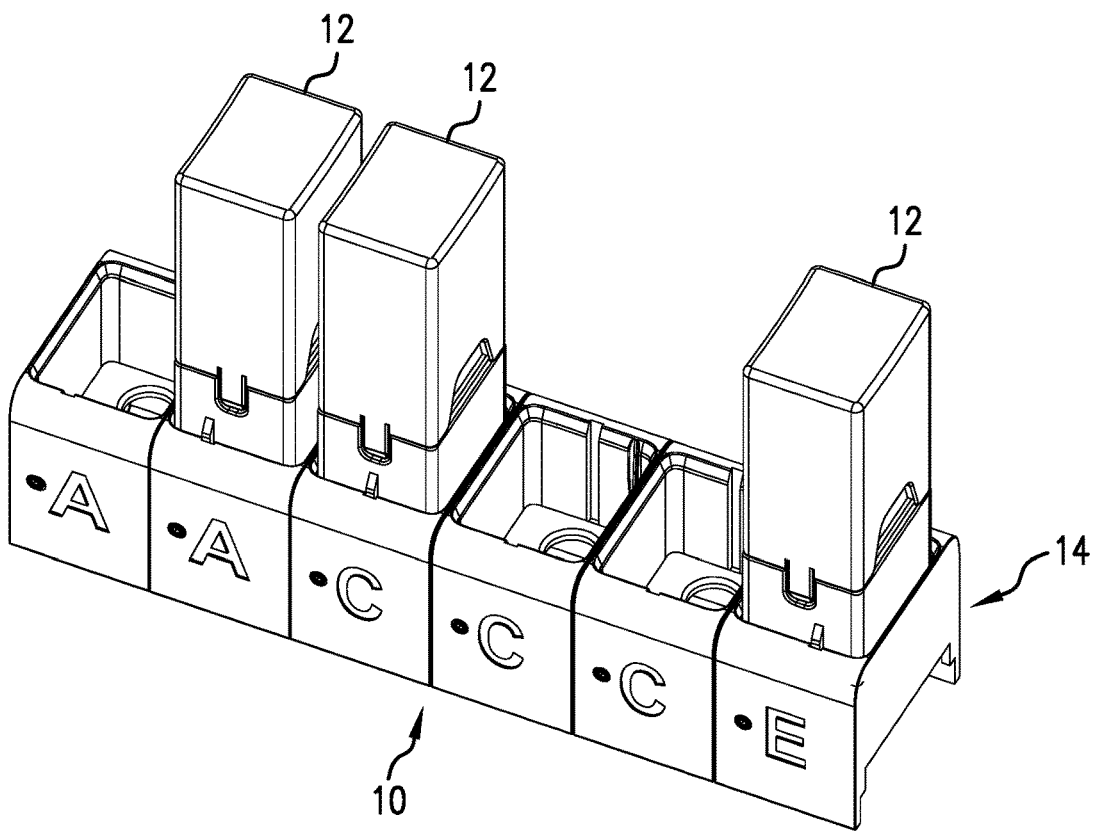
Figure 24:
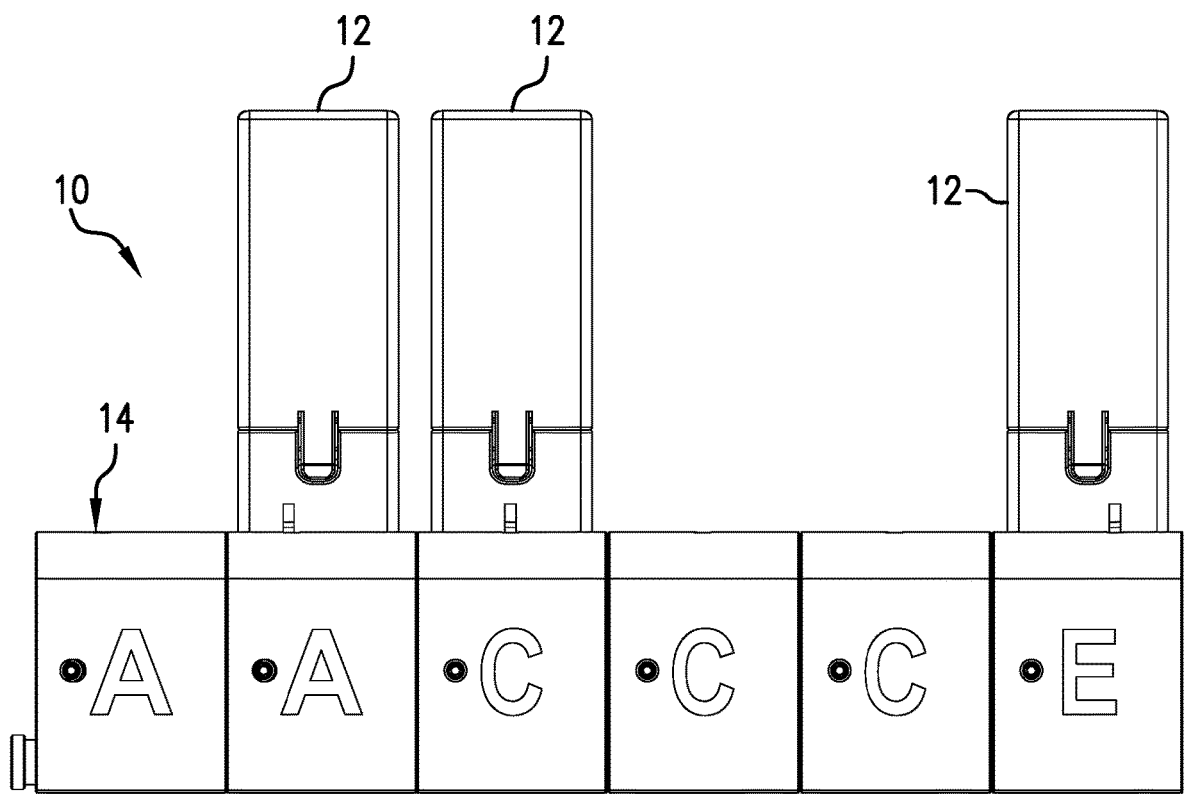
Figure 25:
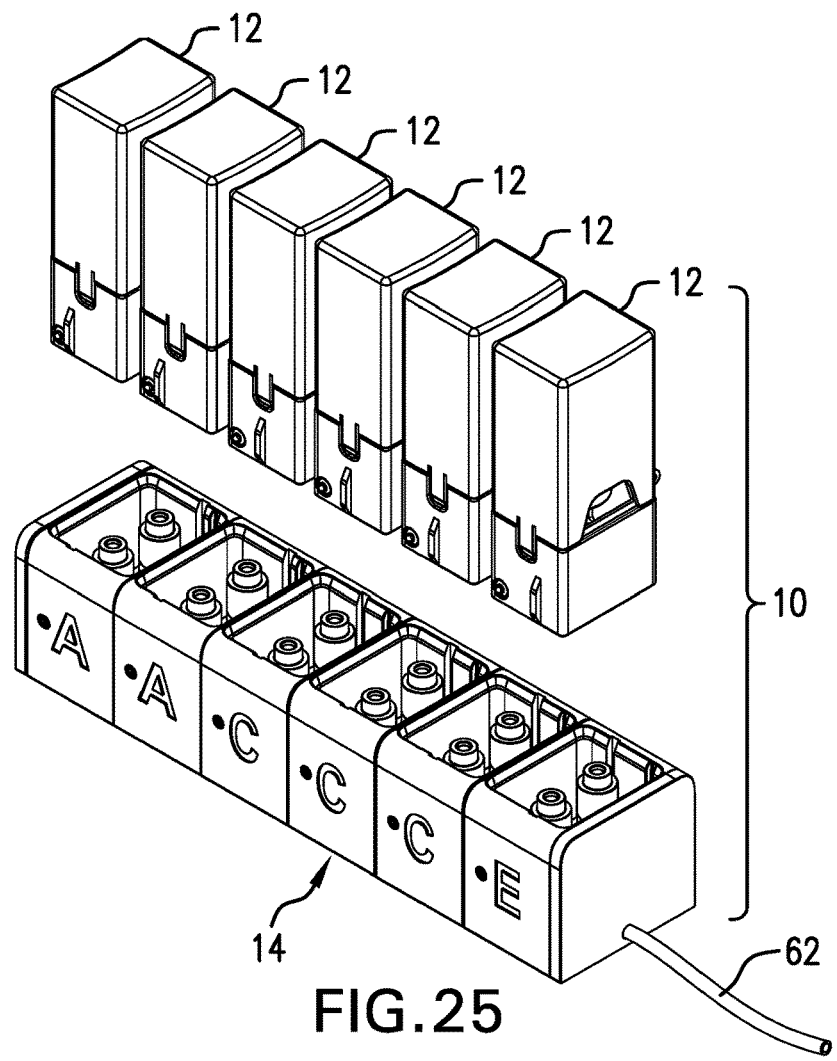
Figure 26:
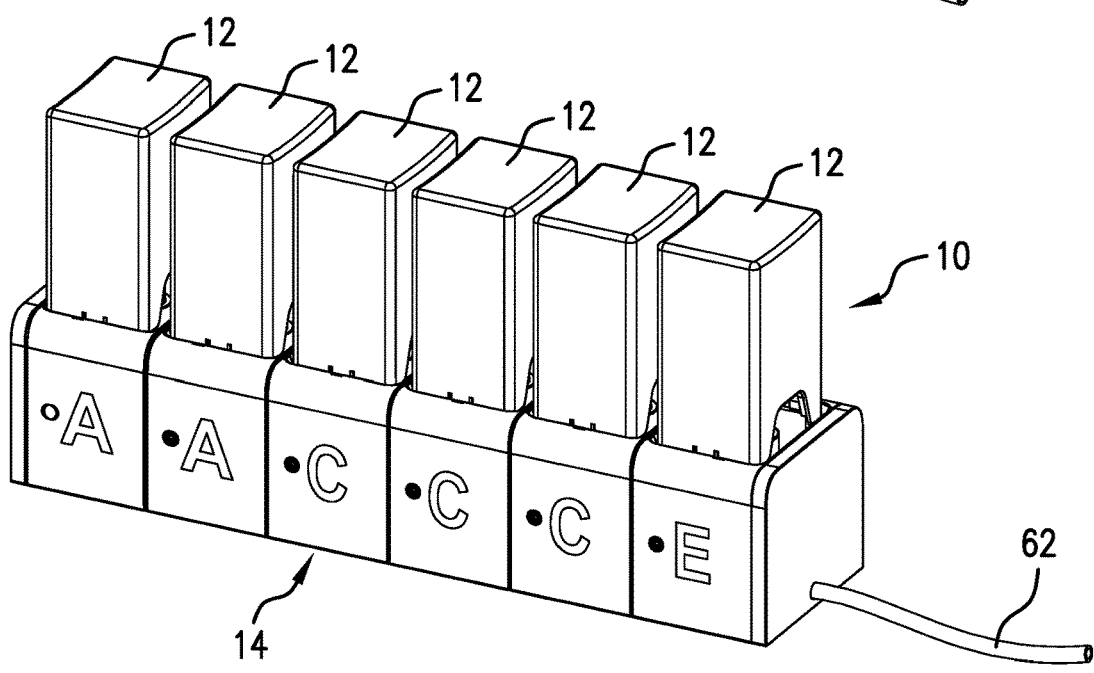
Figure 27:
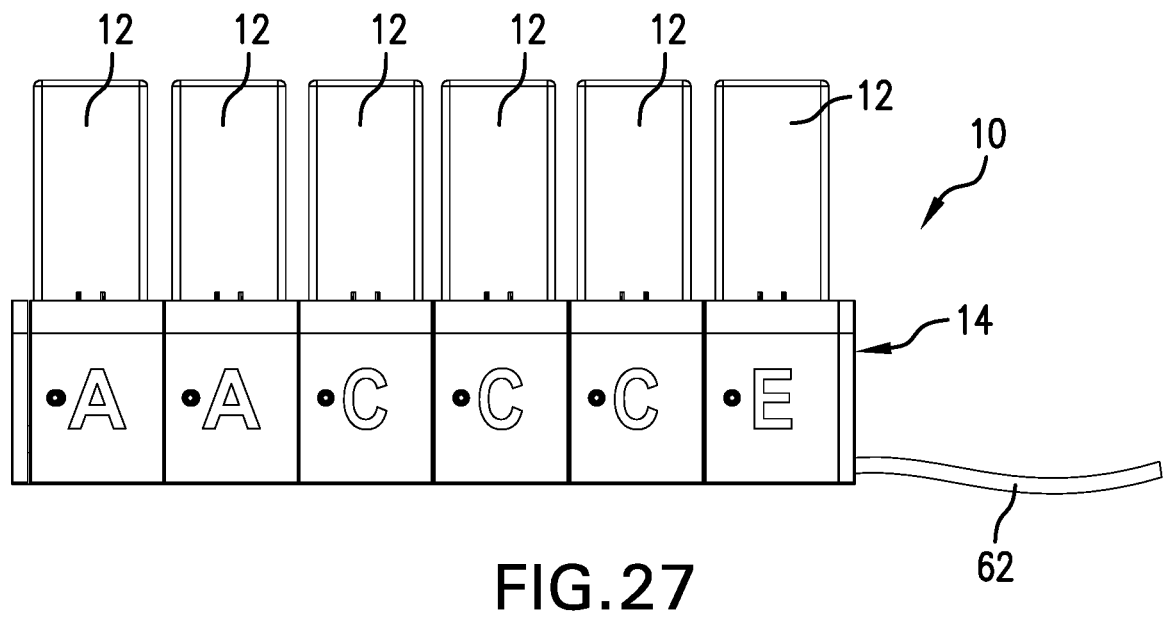

As shown in FIGS. 8-9 and 17-19, as a module 12 is installed into the correct well 32, the inlet ports 48 will contact the vial spike plate 34 within the module 12 through the openings 50. As best shown in FIG. 8, the vial spike plate 34 is releasably retained in an initial state adjacent the openings 50 by cooperating retention elements formed on the vial spike plate 34, e.g., deflectable detents 51a, and the lid 18, e.g., retaining ridge or channel 51b. In the initial state, the ports 46 are axially aligned with the openings 50 so as to be accessible therethrough. As shown in FIGS. 17-19, with insertion of the module 12 into the well 32, the inlet ports 48 engage the ports 46 to create sealed fluid flow paths therebetween with the ports 46 causing the check valving 52 to open. Further insertion of the module 12, causes the lid 12 to move relative to the vial spike plate 34, which is held stationary by the inlet ports 48. With relative movement, the holding force of the cooperating retention elements may be overcome with the body 16 moving toward the vial spike plate 34 where, upon sufficient movement, the spike 36 pierces the septum 38. The module 12 can be locked in the well 32 to ensure connection with the spike 36 and to limit re-usability of the module 12. Movement of the vial spike plate 34 through the lid 18 may be guided by channels or other structures. Once all modules 12 are installed a fluidic circuit from the main line, through all drug vials 22, and ending at the vent 60 will be complete allowing the evacuation of all modules' drug vial contents.

Liquid may be drawn from the drug vials 22 to be delivered through the common outlet 58 into an outlet tube 62. This allows for different liquid drugs to be accommodated by the drug vials 22 of the modules 12 with the liquid drugs being combined by the device 10. As will be appreciated by those skilled in the art, any quantity of the modules 12 may be utilized, possibly limited by the fluidic resistance of the assembly and/or strength of negative pressure utilized with the assembly.

Figure 10:
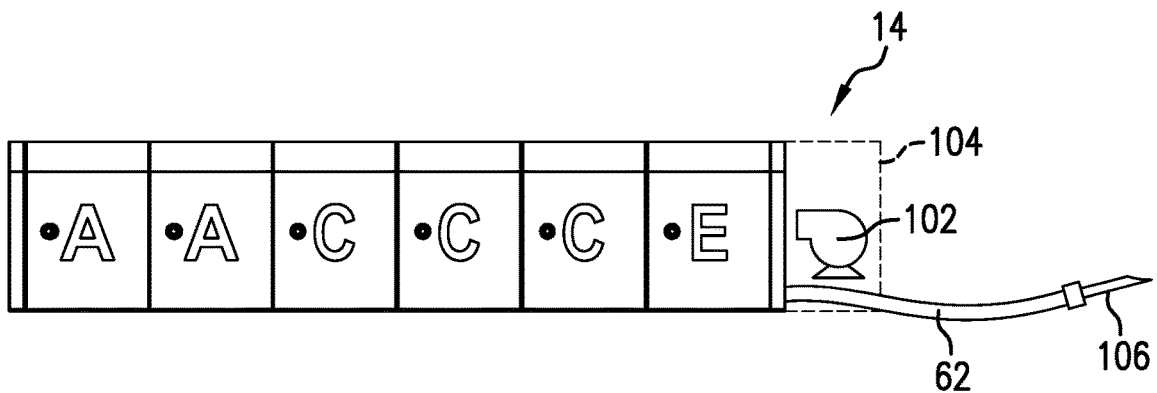
FIGS. 10-13 show a base tray useable with the subject invention.
Figure 11:
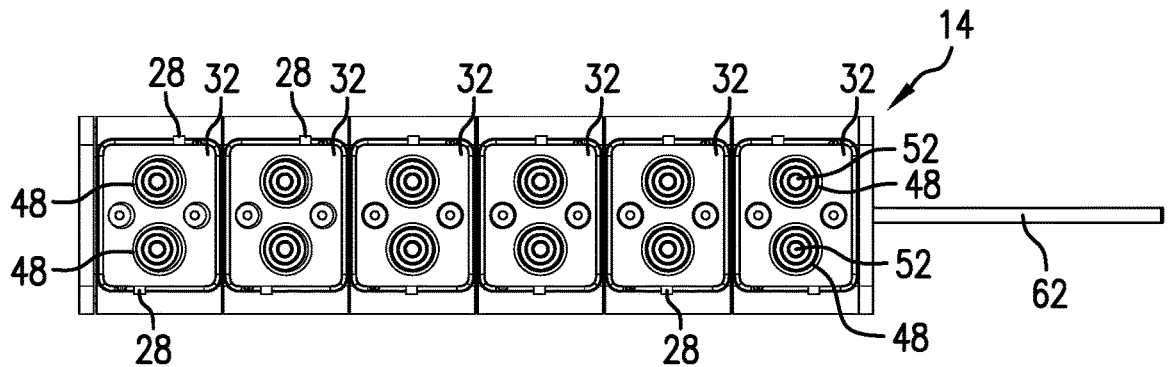

A source of negative pressure (e.g., pump) is required to draw the liquid drugs through the modules 12. Negative pressure may be provided by an external pump 100 (e.g., a syringe) or an internal pump 102 in communication (directly or indirectly) with the common outlet 58 and/or the outlet tube 62 to convey discharged liquid drug to a target delivery site, such as an IV bag, drug container, or directly into a patient. As shown in FIG. 10, the base tray 10 may be optionally provided with a housing 104, with the outlet tube 62 located at least partially therein. The internal pump 102 may be provided in the housing 102, along with any motor, power source, controller, etc., useable to operate and/or control the internal pump 102. A cannula 106, as known in the art, may be provided on the outlet tube 62 as needed for injection or other accessing. Sufficient negative pressure needs to be generated to draw fully the contents of all of the drug vials 22. Check valving may be provided along the common outlet 58 and/or the outlet tube 62 to limit back flow. The external pump 100 and/or the internal pump 102 may be non-contact pumps, e.g., peristaltic pumps, which may act on the outlet tube 62 without contacting the liquid flow therethrough.

One or more of the drug vials 22 may contain lyophilized drug which may be reconstituted with introduction of a diluent. A diluent may be located upstream from the lyophilized drug such that the diluent is drawn into the drug vial with the lyophilized drug with reconstituted drug being drawn therefrom. Various drugs may be contained in the drug vials. Diluents or other additives may be contained as well to increase the efficacy of the drug combination to be delivered.

In one embodiment, the drug delivery device 10 is able to deliver two or more drugs for the benefit of the patient suffering from any of a wide range of diseases or conditions, e.g., cancer, autoimmune disorder, inflammatory disorder, cardiovascular disease or fibrotic disorder.

In one embodiment, one or more of the drugs of the drug delivery device 10 is an immune checkpoint inhibitor. In certain embodiments, the immune checkpoint inhibitor is Programmed Death-1 ("PD-1") pathway inhibitor, a cytotoxic T-lymphocyte-associated antigen 4 ("CTLA-4") antagonist, a Lymphocyte Activation Gene-3 ("LAG3") antagonist, a CD80 antagonist, a CD86 antagonist, a T cell immunoglobulin and mucin domain ("Tim-3") antagonist, a T cell immunoreceptor with Ig and ITIM domains ("TIGIT") antagonist, a CD20 antagonist, a CD96 antagonist, a Indoleamine 2,3-dioxygenase ("IDO1") antagonist, a stimulator of interferon genes ("STING") antagonist, a GARP antagonist, a CD40 antagonist, Adenosine A2A receptor ("A2aR") antagonist, a CEACAM1 (CD66a) antagonist, a CEA antagonist, a CD47 antagonist, a Receptor Related Immunoglobulin Domain Containing Protein ("PVRIG") antagonist, a tryptophan 2,3-dioxygenase ("TDO") antagonist, a V-domain Ig suppressor of T cell activation ("VISTA") antagonist, or a Killer-cell Immunoglobulin-like Receptor ("KIR") antagonist.

In one embodiment, the PD-1 pathway inhibitor is an anti-PD-1 antibody or antigen binding fragment thereof. In certain embodiments, the anti-PD-1 antibody is pembrolizumab (KEYTRUDA; MK-3475), pidilizumab (CT-011), nivolumab (OPDIVO; BMS-936558), PDR001, MEDI0680 (AMP-514), TSR-042, REGN2810, JS001, AMP-224 (GSK-2661380), PF-06801591, BGB-A317, BI 754091, or SHR-1210.

In one embodiment, the PD-1 pathway inhibitor is an anti-PD-L1 antibody or antigen binding fragment thereof. In certain embodiments, the anti-PD-L1 antibody is atezolizumab (TECENTRIQ; RG7446; MPDL3280A; RO5541267), durvalumab (MEDI4736), BMS-936559, avelumab (bavencio), LY3300054, CX-072 (Proclaim-CX-072), FAZ053, KN035, or MDX-1105.

In one embodiment, the PD-1 pathway inhibitor is a small molecule drug. In certain embodiments, the PD-1 pathway inhibitor is CA-170. In another embodiment, the PD-1 pathway inhibitor is a cell based therapy. In one embodiment, the cell based therapy is a MiHA-loaded PD-L1/L2-silenced dendritic cell vaccine. In other embodiments, the cell based therapy is an anti-programmed cell death protein 1 antibody expressing pluripotent killer T lymphocyte, an autologous PD-1-targeted chimeric switch receptor-modified T lymphocyte, or a PD-1 knockout autologous T lymphocyte.

In one embodiment, the PD-1 pathway inhibitor is an anti-PD-L2 antibody or antigen binding fragment thereof. In another embodiment, the anti-PD-L2 antibody is rHIgM12B7.

In one embodiment, the PD-1 pathway inhibitor is a soluble PD-1 polypeptide. In certain embodiments, the soluble PD-1 polypeptide is a fusion polypeptide. In some embodiments, the soluble PD-1 polypeptide comprises a ligand binding fragment of the PD-1 extracellular domain. In other embodiments, the soluble PD-1 polypeptide comprises a ligand binding fragment of the PD-1 extracellular domain. In another embodiment, the soluble PD-1 polypeptide further comprises an Fc domain.

In one embodiment, the immune checkpoint inhibitor is a CTLA-4 antagonist. In certain embodiments, the CTLA-4 antagonist is an anti-CTLA-4 antibody or antigen binding fragment thereof. In some embodiments, the anti-CTLA-4 antibody is ipilimumab (YERVOY), tremelimumab (ticilimumab; CP-675,206), AGEN-1884, or ATOR-1015. In one embodiment, the drug delivery device 10 includes a CTLA-4 antagonist, e.g., ipilimumab (YERVOY), a PD-1 pathway inhibitor, e.g., nivolumab (OPDIVO) or pembrolizumab (KEYTRUDA).

In one embodiment, the immune checkpoint inhibitor is an antagonist of LAG3. In certain embodiments, the LAG3 antagonist is an anti-LAG3 antibody or antigen binding fragment thereof. In certain embodiments, the anti-LAG3 antibody is relatlimab (BMS-986016), MK-4280 (28G-10), REGN3767, GSK2831781, IMP731 (H5L7BW), BAP050, IMP-701 (LAG-5250), IMP321, TSR-033, LAG525, BI 754111, or FS-118. In one embodiment, the drug delivery device 10 includes a LAG3 antagonist, e.g., relatlimab or MK-4280, and a PD-1 pathway inhibitor, e.g., nivolumab (OPDIVO) or pembrolizumab (KEYTRUDA). In one embodiment, the drug delivery device 10 includes a LAG3 antagonist, e.g., relatlimab or MK-4280, and a CTLA-4 antagonist, e.g., ipilimumab (YERVOY). In one embodiment, the drug delivery device 10 includes a LAG3 antagonist, e.g., relatlimab or MK-4280, a CTLA-4 antagonist, e.g., ipilimumab (YERVOY), and a PD-1 pathway inhibitor, e.g., nivolumab (OPDIVO) or pembrolizumab (KEYTRUDA).

In one embodiment, the CTLA-4 antagonist is a soluble CTLA-4 polypeptide. In one embodiment, the soluble CTLA-4 polypeptide is abatacept (ORENCIA), belatacept (NULOJIX), RG2077, or RG-1046. In another embodiment, the CTLA-4 antagonist is a cell based therapy. In some embodiments, the CTLA-4 antagonist is an anti-CTLA4 mAb RNA/GITRL RNA-transfected autologous dendritic cell vaccine or an anti-CTLA-4 mAb RNA-transfected autologous dendritic cell vaccine.

In one embodiment, the immune checkpoint inhibitor is a KIR antagonist. In certain embodiments, the KIR antagonist is an anti-KIR antibody or antigen binding fragment thereof. In some embodiments, the anti-KIR antibody is lirilumab (1-7F9, BMS-986015, IPH 2101) or IPH4102.

In one embodiment, the immune checkpoint inhibitor is TIGIT antagonist. In one embodiment, the TIGIT antagonist is an anti-TIGIT antibody or antigen binding fragment thereof. In certain embodiments, the anti-TIGIT antibody is BMS-986207, AB 154, COM902 (CGEN-15137), or OMP-313M32.

In one embodiment, the immune checkpoint inhibitor is Tim-3 antagonist. In certain embodiments, the Tim-3 antagonist is an anti-Tim-3 antibody or antigen binding fragment thereof. In some embodiments, the anti-Tim-3 antibody is TSR-022 or LY3321367.

In one embodiment, the immune checkpoint inhibitor is an IDO1 antagonist. In another embodiment, the IDO1 antagonist is indoximod (NLG8189; 1-methyl-D-TRP), epacadostat (INCB-024360, INCB-24360), KHK2455, PF-06840003, navoximod (RG6078, GDC-0919, NLG919), BMS-986205 (F001287), or pyrrolidine-2,5-dione derivatives.

In one embodiment, the immune checkpoint inhibitor is a STING antagonist. In certain embodiments, the STING antagonist is 2' or 3'-mono-fluoro substituted cyclic-di-nucleotides; 2'3'-di-fluoro substituted mixed linkage 2',5'-3', 5' cyclic-di-nucleotides; 2'-fluoro substituted, bis-3',5' cyclic-di-nucleotides; 2',2"-diF-Rp,Rp,bis-3',5' cyclic-di-nucleotides; or fluorinated cyclic-di-nucleotides.

In one embodiment, the immune checkpoint inhibitor is CD20 antagonist. In some embodiments, the CD20 antagonist is an anti-CD20 antibody or antigen binding fragment thereof. In one embodiment, the anti-CD20 antibody is rituximab (RITUXAN; IDEC-102; IDEC-C2B8), ABP 798, ofatumumab, or obinutuzumab.

In one embodiment, the immune checkpoint inhibitor is CD80 antagonist. In certain embodiments, the CD80 antagonist is an anti-CD80 antibody or antigen binding fragment thereof. In one embodiment, the anti-CD80 antibody is galiximab or AV 1142742.

In one embodiment, the immune checkpoint inhibitor is a GARP antagonist. In some embodiments, the GARP antagonist is an anti-GARP antibody or antigen binding fragment thereof. In certain embodiments, the anti-GARP antibody is ARGX-115.

In one embodiment, the immune checkpoint inhibitor is a CD40 antagonist. In certain embodiments, the CD40 antagonist is an anti-CD40 antibody for antigen binding fragment thereof. In some embodiments, the anti-CD40 antibody is BMS3h-56, lucatumumab (HCD122 and CHIR-12.12), CHIR-5.9, or dacetuzumab (huS2C6, PRO 64553, RG 3636, SGN 14, SGN-40). In another embodiment, the CD40 antagonist is a soluble CD40 ligand (CD40-L). In one embodiment, the soluble CD40 ligand is a fusion polypeptide. In one embodiment, the soluble CD40 ligand is a CD40-L/FC2 or a monomeric CD40-L.

In one embodiment, the immune checkpoint inhibitor is an A2aR antagonist. In some embodiments, the A2aR antagonist is a small molecule. In certain embodiments, the A2aR antagonist is CPI-444, PBF-509, istradefylline (KW-6002), preladenant (SCH420814), tozadenant (SYN115), vipadenant (BIIB014), HTL-1071, ST1535, SCH412348, SCH442416, SCH58261, ZM241385, or AZD4635.

In one embodiment, the immune checkpoint inhibitor is a CEACAM1 antagonist. In some embodiments, the CEACAM1 antagonist is an anti-CEACAM1 antibody or antigen binding fragment thereof. In one embodiment, the anti-CEACAM1 antibody is CM-24 (MK-6018).

In one embodiment, the immune checkpoint inhibitor is a CEA antagonist. In one embodiment, the CEA antagonist is an anti-CEA antibody or antigen binding fragment thereof. In certain embodiments, the anti-CEA antibody is cergutuzumab amunaleukin (RG7813, RO-6895882) or RG7802 (RO6958688).

In one embodiment, the immune checkpoint inhibitor is a CD47 antagonist. In some embodiments, the CD47 antagonist is an anti-CD47 antibody or antigen binding fragment thereof. In certain embodiments, the anti-CD47 antibody is HuF9-G4, CC-90002, TTI-621, ALX148, NI-1701, NI-1801, SRF231, or Effi-DEM.

In one embodiment, the immune checkpoint inhibitor is a PVRIG antagonist. In certain embodiments, the PVRIG antagonist is an anti-PVRIG antibody or antigen binding fragment thereof. In one embodiment, the anti-PVRIG antibody is COM701 (CGEN-15029).

In one embodiment, the immune checkpoint inhibitor is a TDO antagonist. In one embodiment, the TDO antagonist is a 4-(indol-3-yl)-pyrazole derivative, a 3-indol substituted derivative, or a 3-(indol-3-yl)-pyridine derivative. In another embodiment, the immune checkpoint inhibitor is a dual IDO and TDO antagonist. In one embodiment, the dual IDO and TDO antagonist is a small molecule.

In one embodiment, the immune checkpoint inhibitor is a VISTA antagonist. In some embodiments, the VISTA antagonist is CA-170 or JNJ-61610588.

In one embodiment, one or more of the drugs of the drug delivery device 10 is an immune checkpoint enhancer or stimulator.

In one embodiment, the immune checkpoint enhancer or stimulator is a CD28 agonist, a 4-1BB agonist, an OX40 agonist, a CD27 agonist, a CD80 agonist, a CD86 agonist, a CD40 agonist, an ICOS agonist, a CD70 agonist, or a GITR agonist.

In one embodiment, the immune checkpoint enhancer or stimulator is an OX40 agonist. In certain embodiments, the OX40 agonist is an anti-OX40 antibody or antigen binding fragment thereof. In some embodiments, the anti-OX40 antibody is tavolixizumab (MEDI-0562), pogalizumab (MOXR0916, RG7888), GSK3174998, ATOR-1015, MEDI-6383, MEDI-6469, BMS 986178, PF-04518600, or RG7888 (MOXR0916). In another embodiment, the OX40 agonist is a cell based therapy. In certain embodiments, the OX40 agonist is a GINAKIT cell (iC9-GD2-CD28-OX40-expressing T lymphocytes).

In one embodiment, the immune checkpoint enhancer or stimulator is a CD40 agonist. In some embodiments, the CD40 agonist is an anti-CD40 antibody or antigen binding fragment thereof. In one embodiment, the anti-CD40 antibody is ADC-1013 (JNJ-64457107), RG7876 (RO-7009789), HuCD40-M2, APX005M (EPI-0050), or Chi Lob 7/4. In another embodiment, the CD40 agonist is a soluble CD40 ligand (CD40-L). In one embodiment, the soluble CD40 ligand is a fusion polypeptide. In certain embodiments, the soluble CD40 ligand is a trimeric CD40-L (AVREND®).

In one embodiment, the immune checkpoint enhancer or stimulator is a GITR agonist. In certain embodiments, the GITR agonist is an anti-GITR antibody or antigen binding fragment thereof. In one embodiment, the anti-GITR antibody is BMS-986156, TRX518, GWN323, INCAGN01876, or MEDI1873. In one embodiment, the GITR agonist is a soluble GITR ligand (GITRL). In some embodiments, the soluble GITR ligand is a fusion polypeptide. In another embodiment, the GITR agonist is a cell based therapy. In one embodiment, the cell based therapy is an anti-CTLA4 mAb RNA/GITRL RNA-transfected autologous dendritic cell vaccine or a GITRL RNA-transfected autologous dendritic cell vaccine.

In one embodiment, the immune checkpoint enhancer or stimulator a 4-1BB agonist. In some embodiments, the 4-1BB agonist is an anti-4-1BB antibody or antigen binding fragment thereof. In one embodiment, the anti-4-1BB antibody is urelumab or PF-05082566.

In one embodiment, the immune checkpoint enhancer or stimulator is a CD80 agonist or a CD86 agonist. In some embodiments, the CD80 agonist or the CD86 agonist is a soluble CD80 or CD86 ligand (CTLA-4). In certain embodiments, the soluble CD80 or CD86 ligand is a fusion polypeptide. In one embodiment, the CD80 or CD86 ligand is CTLA4-Ig (CTLA4-IgG4m, RG2077, or RG1046) or abatacept (ORENCIA, BMS-188667). In other embodiments, the CD80 agonist or the CD86 agonist is a cell based therapy. In one embodiment, the cell based therapy is MGN1601 (an allogeneic renal cell carcinoma vaccine).

In one embodiment, the immune checkpoint enhancer or stimulator is a CD28 agonist. In some embodiments, the CD28 agonist is an anti-CD28 antibody or antigen binding fragment thereof. In certain embodiments, the anti-CD28 antibody is TGN1412.

In one embodiment, the CD28 agonist is a cell based therapy. In certain embodiments, the cell based therapy is JCAR015 (anti-CD19-CD28-zeta modified CAR CD3+ T lymphocyte); CD28CAR/CD137CAR-expressing T lymphocyte; allogeneic CD4+ memory Th1-like T cells/microparticle-bound anti-CD3/anti-CD28; anti-CD19/CD28/CD3zeta CAR gammaretroviral vector-transduced autologous T lymphocytes KTE-C19; anti-CEA IgCD28TCR-transduced autologous T lymphocytes; anti-EGFRvIII CAR-transduced allogeneic T lymphocytes; autologous CD123CAR-CD28-CD3zeta-EGFRt-expressing T lymphocytes; autologous CD171-specific CAR-CD28 zeta-4-1-BB-EGFRt-expressing T lymphocytes; autologous CD19CAR-CD28-CD3zeta-EGFRt-expressing Tcm-enriched T cells; autologous PD-1-targeted chimeric switch receptor-modified T lymphocytes (chimera with CD28); CD19CAR-CD28-CD3zeta-EGFRt-expressing Tcm-enriched T lymphocytes; CD19CAR-CD28-CD3zeta-EGFRt-expressing Tn/mem-enriched T lymphocytes; CD19CAR-CD28zeta-4-1BB-expressing allogeneic T lymphocytes; CD19CAR-CD3zeta-4-1BB-CD28-expressing autologous T lymphocytes; CD28CAR/CD137CAR-expressing T lymphocytes; CD3/CD28 costimulated vaccine-primed autologous T lymphocytes; or iC9-GD2-CD28-OX40-expressing T lymphocytes.

In one embodiment, the immune checkpoint enhancer or stimulator is a CD27 agonist. In certain embodiments, the CD27 agonist is an anti-CD27 antibody or antigen binding fragment thereof. In one embodiment, the anti-CD27 antibody is varlilumab (CDX-1127).

In one embodiment, the immune checkpoint enhancer or stimulator is a CD70 agonist. In some embodiments, the CD70 agonist is an anti-CD70 antibody or antigen binding fragment thereof. In one embodiment, the anti-CD70 antibody is ARGX-110.

In one embodiment, the immune checkpoint enhancer or stimulator is an ICOS agonist. In certain embodiments, the ICOS agonist is an anti-ICOS antibody or antigen binding fragment thereof. In some embodiments, the anti-ICOS antibody is BMS986226, MEDI-570, GSK3359609, or JTX-2011. In other embodiments, the ICOS agonist is a soluble ICOS ligand. In some embodiments, the soluble ICOS ligand is a fusion polypeptide. In one embodiment, the soluble ICOS ligand is AMG 750.

In one embodiment, one or more of the drugs of the drug delivery device 10 is an anti-CD73 antibody or antigen binding fragment thereof. In certain embodiments, the anti-CD73 antibody is MEDI9447.

In one embodiment, one or more of the drugs of the drug delivery device 10 is a TLR9 agonist. In one embodiment, the TLR9 agonist is agatolimod sodium.

In one embodiment, one or more of the drugs of the drug delivery device 10 is a cytokine. In certain embodiments, the cytokine is a chemokine, an interferon, an interleukin, lymphokine, or a member of the tumor necrosis factor family. In some embodiments, the cytokine is IL-2, IL-15, or interferon-gamma.

In one embodiment, one or more of the drugs of the drug delivery device 10 is a TGF-β antagonist. In some embodiments, the TGF-β antagonist is fresolimumab (GC-1008); NIS793; IMC-TR1 (LY3022859); ISTH0036; trabedersen (AP 12009); recombinant transforming growth factor-beta-2; autologous HPV-16/18 E6/E7-specific TGF-beta-resistant T lymphocytes; or TGF-beta-resistant LMP-specific cytotoxic T-lymphocytes.

In one embodiment, one or more of the drugs of the drug delivery device 10 is an iNOS antagonist. In some embodiments, the iNOS antagonist is N-Acetyle-cysteine (NAC), aminoguanidine, L-nitroarginine methyl ester, or S,S-1,4-phenylene-bis(1,2-ethanediyl)bis-isothiourea).

In one embodiment, one or more of the drugs of the drug delivery device 10 is a SHP-1 antagonist.

In one embodiment, one or more of the drugs of the drug delivery device 10 is a colony stimulating factor 1 receptor ("CSF1R") antagonist. In certain embodiments, the CSF1R antagonist is an anti-CSF1R antibody or antigen binding fragment thereof. In some embodiments, the anti-CSF1R antibody is emactuzumab.

In one embodiment, one or more of the drugs of the drug delivery device 10 is an agonist of a TNF family member. In some embodiments, the agonist of the TNF family member is ATOR 1016, ABBV-621, or Adalimumab.

In one embodiment, one or more of the drugs of the drug delivery device 10 is aldesleukin, bempegaldesleukin, tocilizumab, or MEDI5083. In one embodiment, the delivery device 10 includes bempegaldesleukin and a PD-1 pathway inhibitor, e.g., nivolumab (OPDIVO) or pembrolizumab (KEYTRUDA). In one embodiment, the delivery device 10 includes bempegaldesleukin and a LAG3 antagonist, e.g., relatlimab or MK-4280. In one embodiment, the delivery device 10 includes bempegaldesleukin, a PD-1 pathway inhibitor, e.g., nivolumab (OPDIVO) or pembrolizumab (KEYTRUDA), and a LAG3 antagonist, e.g., relatlimab or MK-4280. In one embodiment, the delivery device 10 includes bempegaldesleukin and a CTLA-4 antagonist, e.g., ipilimumab (YERVOY).

In one embodiment, one or more of the drugs of the drug delivery device 10 is a CD160 (NK1) agonist. In certain embodiments, the CD160 (NK1) agonist is an anti-CD160 antibody or antigen binding fragment thereof. In one embodiment, the anti-CD160 antibody is BY55.

What is claimed is:

1. A combinatorial drug delivery device for delivering a predetermined selection of drug components, each of the drug components being contained in a drug vial, the device comprising:
   a plurality of modules, wherein each of the modules includes:
      a body and a lid collectively defining an interior volume formed to accommodate a drug vial, the lid having access openings;
      a spike plate disposed wholly within the interior volume, the spike plate being movable relative to the lid from an initial state, adjacent to the access openings, to within the interior volume away from the access openings, the spike plate having a protruding cannula, terminating at a free end, and first and second ports, first and second openings being formed in the free end with first and second lumens extending therefrom, through the cannula and terminating at the first and second ports, respectively; and,
   a base tray including:
      a framework defining a plurality of wells, each of the wells formed to insertingly receive one of the modules;
      for each of the wells, first and second inlet ports formed to interface with the first and second ports of the module being received in the respective well;
      passageways to connect the second inlet ports of certain wells with the first inlet ports of wells adjacent to the certain wells to permit fluid flow therebetween,
   wherein, for each of the wells, the first and second inlet ports being configured to maintain the spike plate of the respective module in a stationary position with the module being inserted into the well, wherein, for each of the wells, with the respective module being inserted into the well, the first and second inlet ports engage the first and second ports of the spike plate, through the access openings, to create sealed flow paths therebetween, and, wherein, with the spike plate of the respective module in the stationary position and with the module being inserted into the well, for the respective module, the lid moves relative to the spike plate thereby causing the spike plate to move away from the access openings of the lid.

2. A drug delivery device as in claim 1, further comprising a source of negative pressure to draw the drug components from the modules.

3. A drug delivery device as in claim 2, wherein the base tray includes a housing, the source of negative pressure being located in the housing.

4. A drug delivery device as in claim 1, wherein the spike plate is releasably retained in the initial state.

5. A drug delivery device as in claim 1, wherein, a first fluid path is defined extending from the first inlet port, through the first port, through the first lumen, and terminating at the first opening of the cannula, and, wherein, a second fluid path is defined from the second opening of the cannula, through the second lumen, through the second port and to the second inlet port.

6. A drug delivery device as in claim 1, wherein, at least one of the modules further comprising a drug vial accommodated within the interior volume, the drug vial having a septum, wherein, with sufficient insertion of the respective module into the well, the cannula of the spike plate fully pierces the septum of the drug vial.

7. A drug delivery device as in claim 1, wherein the lid is hingedly attached to the body.

8. A combinatorial drug delivery device for delivering a predetermined selection of drug components, each of the drug components being contained in a drug vial, the device comprising:
- a plurality of modules, wherein each of the modules includes a body having an interior volume formed to accommodate a drug vial, a plurality of keying features being defined on the body; and,
- a base tray including a framework defining a plurality of wells bounded by upstanding walls, each of the wells formed to insertingly receive one of the modules, wherein tray keying features are defined on interior portions of the upstanding walls,
- wherein, the keying features and the tray keying features are varied so as to be configured to permit insertion of the modules into predetermined wells to arrange the modules in a predetermined sequence along the base tray, with the keying features and the tray keying features restricting insertion of the modules into the wells which are not predetermined for the modules.

9. A drug delivery device as in claim 8, wherein the keying features include one or more ridges and channels.

10. A drug delivery device as in claim 9, wherein the tray keying features includes one or more ridges and channels.

* * * * *